United States Patent
Ladiwala et al.

(10) Patent No.: US 9,102,709 B1
(45) Date of Patent: Aug. 11, 2015

(54) REGENERATION OF CHROMATOGRAPHY MATERIAL

(75) Inventors: Asif Ladiwala, Natick, MA (US); John Pieracci, Winchester, MA (US)

(73) Assignee: Biogen MA Inc., Cambridge, MA (US)

( * ) Notice: Subject to any disclaimer, the term of this patent is extended or adjusted under 35 U.S.C. 154(b) by 155 days.

(21) Appl. No.: 13/543,650

(22) Filed: Jul. 6, 2012

Related U.S. Application Data

(60) Provisional application No. 61/505,736, filed on Jul. 8, 2011.

(51) Int. Cl.
*A61K 38/00* (2006.01)
*C07K 1/22* (2006.01)
*B08B 3/04* (2006.01)
*C07K 1/14* (2006.01)
*B01D 15/38* (2006.01)
*B08B 3/08* (2006.01)

(52) U.S. Cl.
CPC ... *C07K 1/22* (2013.01); *B08B 3/04* (2013.01); *B01D 15/3809* (2013.01); *B08B 3/08* (2013.01); *C07K 1/14* (2013.01)

(58) Field of Classification Search
None
See application file for complete search history.

(56) References Cited

U.S. PATENT DOCUMENTS

| 6,972,327 | B1 | 12/2005 | Madani et al. |
| 7,052,609 | B2 * | 5/2006 | Braunger et al. ............. 210/656 |
| 2005/0147603 | A1 * | 7/2005 | Smith et al. ................ 424/131.1 |
| 2008/0230478 | A1 | 9/2008 | Johansson et al. |

FOREIGN PATENT DOCUMENTS

WO   WO 0127623 A2 *   4/2001

* cited by examiner

*Primary Examiner* — Daniel E Kolker
*Assistant Examiner* — James Rogers
(74) *Attorney, Agent, or Firm* — Wolf, Freenfield & Sacks, P.C.

(57) ABSTRACT

Methods and kits for regenerating antibody binding resins are provided. In some embodiments the methods include a first step of washing an antibody binding resin with a reducing solution, followed by a second step of washing the antibody binding resin with a chaotropic solution.

22 Claims, 20 Drawing Sheets

Figure 2

| | |
|---|---|
| AA: 0.1 M Na Citrate, pH 2.5 | KA: 12% PEG 400 |
| AB: 0.2 M Na Citrate, pH 2.0 | KB: 12% PEG 400/0.5 M NaCl |
| BA: 0.85% Phosphoric Acid, pH 1.5 | KC: 12% PEG 400/1.0 M NaCl |
| CA: 15 mM Phosphoric acid/0.5 M NaCl, pH 2.0 | KD: 12% PEG 400/0.2 M Na Citrate, pH 2.0 |
| DA: 100 mM thioglycerol, pH 3.7 | LA: 12% PEG 8000 |
| EA: 4 M Urea/50 mM Na Acetate, pH 5.0 | LB: 12% PEG 8000/0.5 M NaCl |
| FA: 2 M Guanidine-HCl, pH 6.5 | LC: 12% PEG 8000/1.0 M NaCl |
| FB: 4 M Guanidine-HCl, pH 6.5 | LD: 12% PEG 8000/0.2 M Na Citrate, pH 2.0 |
| FC: 6 M Guanidine-HCl, pH 6.7 | |
| GA: PAB: 120 mM Phosphoric acid/167 mM Acetic acid/2.2% Benzyl alcohol, pH 1.6 | MA: 0.5% Tween-20 |
| | MB: 1.0% Tween-20 |
| | MC: 0.5% Tween-20/1 M NaCl |
| HA: 20% EtOH/0.5 M Acetic acid, pH 2.7 | MD: 1.0% Tween-20/1 M NaCl |
| HB: 20% EtOH/2.0 M Acetic acid, pH 2.4 | ME: 0.5% Tween-20/0.2 M Na Citrate, pH 2.0 |
| IA: 10% hexylene glycol | |
| IB: 20% hexylene glycol | MF: 1.0% Tween-20/0.2 M Na Citrate, pH 2.0 |
| IC: 10% hexylene glycol/0.5 M NaCl | |
| ID: 20% hexylene glycol/0.5 M NaCl | MG: 0.5% Tween-20/0.5 M Na Acetate, pH 4.6 |
| IE: 10% hexylene glycol/0.2 M Na Citrate, pH 2.0 | |
| | MH: 1.0% Tween-20/0.5 M Na Acetate, pH 4.6 |
| IF: 20% hexylene glycol/0.2 M Na Citrate, pH 2.0 | NA: 1.0% Triton X-100 |
| JA: 10% propylene glycol | NB: 1.0% Triton X-100/1 M NaCl |
| JB: 20% propylene glycol | NC: 1.0% Triton X-100/0.2 M Na Citrate, pH 2.0 |
| JC: 10% propylene glycol/0.5 M NaCl | |
| JD: 20% propylene glycol/0.5 M NaCl | OA: 0.5% Tween-80/0.2 M Na Citrate, pH 2.0 |
| JE: 10% propylene glycol/1.0 M NaCl | |
| JF: 20% propylene glycol/1.0 M NaCl | OB: 1.0% Tween-80/0.2 M Na Citrate, pH 2.0 |
| JG: 10% propylene glycol/0.2 M Na Citrate, pH 2.0 | |
| JH: 20% propylene glycol/0.2 M Na Citrate, pH 2.0 | |

Figure 4

AA: 0.1 M Na Citrate, pH 2.5
AB: 0.2 M Na Citrate, pH 2.0
BA: 0.85% Phosphoric Acid, pH 1.5
CA: 15 mM Phosphoric acid/0.5 M NaCl, pH 2.0
DA: 100 mM thioglycerol, pH 3.7
DB: 100 mM 2-BME
DC: 100 mM DTT
DD: 100 mM L-glutathione reduced
EA: 4 M Urea/50 mM Na Acetate, pH 5.0
FA: 2 M Guanidine-HCl, pH 6.5
FB: 4 M Guanidine-HCl, pH 6.5
FC: 6 M Guanidine-HCl, pH 6.7
FD: 4 M Guanidine acetate, pH 5.8

GA: PAB: 120 mM Phosphoric acid/167 mM Acetic acid/2.2% Benzyl alcohol, pH 1.6
IE: 10% hexylene glycol/0.2 M Na Citrate, pH 2.0
IF: 20% hexylene glycol/0.2 M Na Citrate, pH 2.0
JG: 10% propylene glycol/0.2 M Na Citrate, pH 2.0
JH: 20% propylene glycol/0.2 M Na Citrate, pH 2.0
KD: 12% PEG 400/0.2 M Na Citrate, pH 2.0
ME: 0.5% Tween-20/0.2 M Na Citrate, pH 2.0
MF: 1.0% Tween-20/0.2 M Na Citrate, pH 2.0
NC: 1.0% Triton X-100/0.2 M Na Citrate, pH 2.0
OA: 0.5% Tween-80/0.2 M Na Citrate, pH 2.0
OB: 1.0% Tween-80/0.2 M Na Citrate, pH 2.0
PA: 0.5 M L-Arginine, pH 6.75
PB: 2 M L-Arginine, pH 6.85

Figure 6

| Parameter | EHS + CoGs Recommendation | | | CoGs Recommendation | | Best-in-Class, but corrosive |
|---|---|---|---|---|---|---|
| | Thioglycerol | 2-Mercaptoethanol | 1,4-Dithiothreitol | Urea | Guanidine Acetate | Guanidine HCl |
| CAS | 96-27-5 | 60-24-2 | 3483-12-3 | 57-13-6 | 593-87-3 | 50-01-1 |
| Formula | $C_3H_8O_2S$ | $C_2H_6OS$ | $C_4H_{10}O_2S_2$ | $CH_4N_2O$ | | $CH_5N_3 \cdot HCl$ |
| | ← Reducing Agents → | | | ← Chaotropic Agents → | | |
| Hazard Rating | Health: 2 Flammability: 1 | Health: 3 Flammability: 2 | Health: 2 Flammability: 1 | Health: 2 Flammability: 1 | Health: 0 Flammability: 0 | Health: 2 Flammability: 1 |
| Flashpoint | 113°C | 68°C | 113°C | | | |
| Melting Point | | -50°C | 40-44°C | 133°C | 226-230°C | 180-185°C |
| Boiling Point | 118°C | 157°C | 125-130°C | | | |
| Autoignition Temp | | 295°C | | | | |
| Other | Strong odor; slightly soluble in water | Strong odor. Irritation to eyes, nose, and skin. Extremely destructive if inhaled | Known as Cleland's Reagent, used for protecting SH groups. | Water solutions slowly hydrolyze to ammonium carbonate, and then to ammonia and $CO_2$. | | |
| Toxicity to Daphnia | | EC50 = 0.89-1.52 mg/L | LC50=27 mg/L | EC50=>3,000 mg/L | | |
| Biodegradation | | Not readily biodegradable | | Readily biodegradable | | Not readily biodegradable |
| Estimated TN per Cleaning Event (lb) | 0 | 0 | 0 | 501 | 376 | 376 |

REGENERATION OF CHROMATOGRAPHY MATERIAL

RELATED APPLICATIONS

The present application claims the benefit under 35 U.S.C. 119(e) of the filing date of U.S. Provisional Patent Application 61/505,736, filed on Jul. 8, 2011, the disclosure of which is incorporated herein in its entirety.

FIELD OF THE INVENTION

The invention is in the field of protein purification chromatography, particularly the use of affinity chromatography resins such as, for example, protein A chromatography resins.

BACKGROUND

Protein A affinity chromatography is frequently the method of choice to purify antibodies and other Fc-containing proteins (see "Purification Tools for Monoclonal Antibodies" by P. Gagnon, 1996, Validated Biosystems, Inc., Tucson, Ariz., Chapt. 9, Protein A Affinity Chromatography). A preparation containing antibodies is loaded onto a Protein A affinity chromatography resin, washed, and eluted, usually with either a low or high pH buffer. Purification as high as 95% in one step can be achieved.

The price of Protein A affinity chromatography resins is many times the cost of non-affinity supports. In a commercial manufacturing process, this raw material cost can significantly add to the cost of goods. Protein A affinity chromatography resins can be recycled in order to reduce the cost of raw materials. Typically, Protein A affinity chromatography resins are recycled by treatment with strong chaotropic solutions (urea and guanidine hydrochloride), or strongly acidic solutions (such as acetic acid), or a combination thereof. However, these recycling methods often lead to a decrease in column performance Additional methods of regenerating chromatography materials, such as protein A resin are needed therefore.

SUMMARY OF THE INVENTION

In one aspect, the disclosure provides methods for regenerating chromatography resins. In some embodiments, the method include a first step of washing the chromatography resin with a reducing solution followed by a second step of washing the chromatography resin with a chaotropic solution.

In one aspect the disclosure provides a method for regenerating an antibody binding resin, the method comprising a first step of washing an antibody binding resin with a reducing solution, followed by a second step of washing the antibody binding resin with a chaotropic solution, thereby regenerating the antibody binding resin, wherein the first step and the second step are performed separately.

In some embodiments of any of the methods provided herein, the method further comprises a step of washing the antibody binding resin with an equilibration buffer, wherein the step of washing with the equilibration buffer is a separate step that is performed after the first washing step and prior to the second washing step.

In some embodiments of any of the methods provided herein, the method further comprises washing the chromatography resin (e.g., antibody binding resin) with an acidic solution, wherein the step of washing with the acidic solution is a separate step that is performed prior to the first washing step. However, it should be appreciated that the acid washing can be performed after the first washing step described herein (e.g., after one or more of the reducing and/or chaotropic washing steps described herein) in addition to, or instead of, prior to the first washing step.

In some embodiments of any of the methods provided herein, the method further comprises washing the antibody binding resin with a neutralizing solution, wherein the step of washing with the neutralizing solution is a separate step that is performed after the step of washing with the acidic solution and prior to the first washing step.

In some embodiments of any of the methods provided herein, the method further comprises using the antibody binding resin to purify an antibody.

In some embodiments of any of the methods provided herein, the method further comprises repeating the first and second washing steps.

In one aspect the disclosure provides a kit comprising a reducing solution and a chaotropic solution, wherein the reducing solution and the chaotropic solution are separate solutions.

In some embodiments of any of the kits provided herein, the kit further comprises an equilibration solution, wherein the equilibration solution is a separate solution.

In some embodiments of any of the kits provided herein, the kit further comprises an acidic solution, wherein the acidic solution is a separate solution.

In some embodiments of any of the kits provided herein, the kit further comprises a neutralizing solution, wherein the neutralizing solution is a separate solution.

In some embodiments of any of the methods or kits provided herein, the reducing solution includes a reducing agent selected from the group consisting of thioglycerol, 1-4,-dithiothreitol, and 2-mercaptoethanol. In some embodiments, the reducing agent is thioglycerol.

In some embodiments of any of the methods or kits provided herein, the chaotropic solution includes a chaotropic agent selected from the group consisting of guanidine HCl, urea, and guanidine acetate. In some embodiments, the chaotropic agent is guanidine HCl or urea.

In some embodiments of any of the methods or kits provided herein, the equilibration buffer is selected from the group consisting of phosphate buffers and carbonate buffers. In some embodiments, the equilibration buffer is a phosphate buffer.

In some embodiments of any of the methods or kits provided herein, the acidic solution is selected from the group consisting of phosphoric acid and acetic acid. In some embodiments, the acidic solution is phosphoric acid. However, it should be appreciated that other suitable acids, or a combination of two or more acids, can be used as aspects of the invention are not limited in this respect.

In some embodiments of any of the methods or kits provided herein, the neutralizing solution is selected from the group consisting of phosphate buffers, weak acids and weak bases. In some embodiments, the neutralizing solution is a phosphate buffer.

In some embodiments of any of the methods or kits provided herein, the antibody binding resin is selected from the group consisting of a protein A resin and a protein G resin. In some embodiments, the antibody binding resin is a protein A resin.

BRIEF DESCRIPTION OF THE DRAWINGS

The figures are illustrative only and are not required for enablement of the invention disclosed herein.

FIG. 2 provides an overview of cleaning solutions.

FIG. 4 provides an overview of sequential combinations of lead cleaning solutions.

FIG. 6 shows a selection of lead cleaning agents.

DETAILED DESCRIPTION OF THE INVENTION

Figure 1:
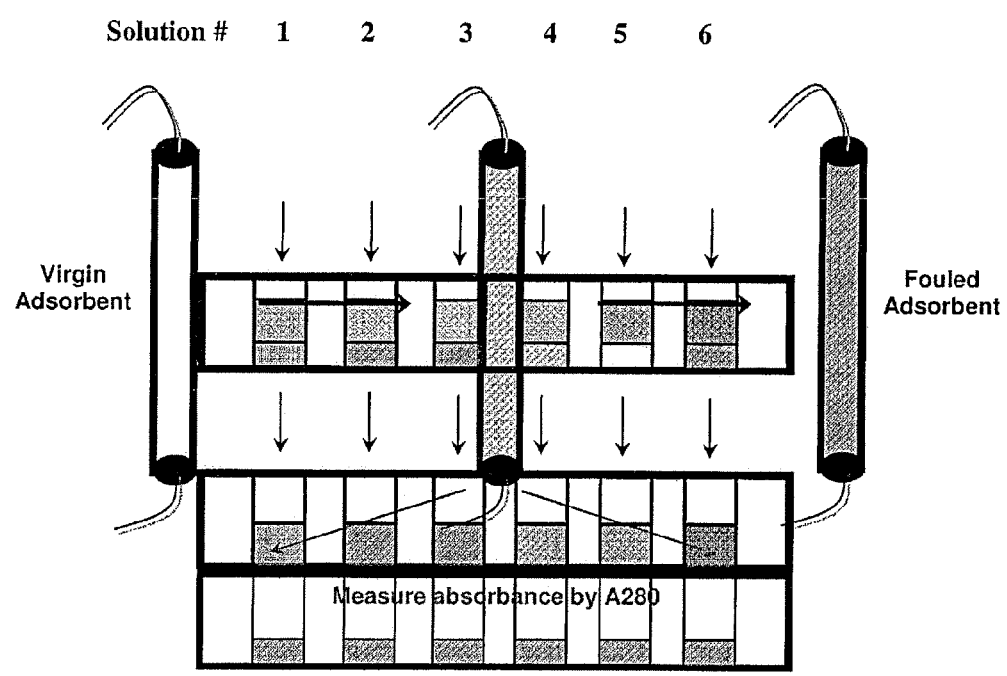
FIG. 1 provides an overview of a batch screening protocol.

The disclosure provides methods of more efficiently regenerating chromatography resins. In particular, the methods are useful for the regeneration of affinity column resins. The methods provide a more efficient cleaning process resulting in increased lifetime of resin material. The more efficient regenerating methods of the disclosure permit extended performance of affinity resins for use in production of proteins including therapeutic proteins.

In one aspect, the disclosure provides a method of regenerating a chromatography resin (e.g., Protein A or Protein G) by washing the chromatography resin with a reducing solution followed by a chaotropic solution. In some embodiments, the resin is washed with an equilibration solution, wherein the wash with the equilibration solution is performed after the wash with the reducing solution and prior to the wash with the chaotropic solution.

In some embodiments, the method includes an initial wash of the column with an acid solution (e.g., 0.85% phosphoric acid), followed by a wash with neutralizing solution to adjust the column to near neutral pH. In some embodiments, the wash with the acid solution and the neutralizing solution are performed prior to the wash with the reducing solution and a subsequent wash with the chaotropic solution. However, additional or alternative acid washing steps may be performed at different stages in a process described herein.

In some embodiments, the method includes an initial wash of the column with an acid solution (e.g., 0.85% phosphoric acid); a wash with a neutralizing solution to adjust the column to near neutral pH); a subsequent wash with a reducing solution; a wash with equilibration solution to wash away the reducing agent from the column, and a final wash with a chaotropic solution In some embodiments, the method uses a reducing solution comprising 100 mM thioglycerol, while the chaotropic solution comprises 4M guanidine hydrochloride or 8M urea.

The reducing solution comprises a reducing agent. In some embodiments, the reducing agent provides a source of free thiols. Reducing agents include but are not limited to reduced glutathione, dithiothreitol (DTT), 2-mercaptoethanol, dithionitrobenzoate (DTNB), cysteine, thioglycerol, or any combination of two or more thereof. However, it should be appreciated that other reducing agents or combinations thereof may be used. In some embodiments, the concentration of reducing agent in the reducing solution is at least 1 mM, at least 2 mM, at least 5 mM, at least 10 mM, at least 20 mM, at least 30 mM, and at least 50 mM, at least 100 mM, at least 200 mM, at least 500 mM or more. The reducing solution may consist only of a reducing agent or may include additional components (e.g., a buffer). It should be appreciated that other reducing agents can be used as aspects of the invention are not limited in this respect. It also should be appreciated that a reducing solution may include a combination of two or more (e.g., 3, 4, 5, 6, 7, 8, 9, 10, etc.) different reducing agents at the same concentration or in different concentrations. However, the reducing solution does not function as a chaotropic solution and does not include significant amounts of a chaotropic agent (e.g., less than 10 mM, less than 5 mM, less than 1 mM, less than 100 µM, less than 10 µM, less than 1 µM, less than 100 nM, less than 10 nM, less than 1 nM, less than 100 pM, less than 10 pM, less than 1 pM, or less chaotropic agent, for example substantially no chaotropic agent, or no chaotropic agent).

Chaotropic solutions comprise a chaotropic agent (e.g., a chaotropic salt). Chaotropic agents include but are not limited to urea, thiourea, guanidine hydrochloride and lithium perchlorate or any combination thereof. In some embodiments, the chaotropic agent in the chaotropic solution is at greater than about 200 mM, greater than about 500 mM, greater than about 1 M, greater than about 2 M, greater than about 3 M, greater than about 4 M, and greater than about 5 M such as, for example, about 6 M. The chaotropic solution may consist only of a chaotropic agent or may include additional components (e.g., a buffer). It should be appreciated that other chaotropic agents can be used as aspects of the invention are not limited in this respect. It also should be appreciated that a chaotropic solution may include a combination of two or more (e.g., 3, 4, 5, 6, 7, 8, 9, 10, etc.) different chaotropic agents at the same concentration or in different concentrations. However, the chaotropic solution does not function as a reducing solution and does not include significant amounts of a reducing agent (e.g., less than 100 µM, less than 10 µM, less than 1 µM, less than 100 nM, less than 10 nM, less than 1 nM, less than 100 pM, less than 10 pM, less than 1 pM, or less reducing agent, for example substantially no reducing agent, or no reducing agent).

Equilibration solutions include an equilibration buffer. Equilibration buffers include but are not limited to phosphate buffers, and carbonate buffers, or any combination thereof, and may include a low salt concentration. However, other buffers, or combinations of buffers, can be used as aspects of the invention are not limited in this respect. In some embodiments, the concentration of the equilibration buffer in the equilibration solution is at least 1 mM, at least 2 mM, at least 5 mM, at least 10 mM, at least 20 mM, at least 30 mM, and at least 50 mM, at least 100 mM, at least 200 mM, at least 500 mM or more. In some embodiments, the equilibration solutions are used to store the resin for a longer period of time. In some embodiments, the equilibration solutions include a small amount of toxin to prevent growth of microorganisms in the resin.

Acid solutions include an acid. In general the acid solutions used in the methods of the invention are relatively mild. The solutions are acidic enough to clean the resin but do not interfere with the functionality of the resin. In some embodiments the acid is phosphoric acid. In some embodiments the acid is 0.85% phosphoric acid.

Neutralizing solutions include a neutralizing agent. In general administration of a neutralizing solution will result in the column returning to a "neutral" environment. Thus, the neutralization solution may return a column that had been at acidic pH back to neutral pH. In some embodiments the neutralization solution exerts its neutralizing effect by replacing the prior solution. In some embodiments the neutralization solution exerts its neutralizing effect by reacting with the prior buffer (e.g., an acid-base reaction resulting in a pH neutral environment). In some embodiments, the neutralizing solution has a similar composition as the equilibrium solution.

A column to be regenerated is typically washed with at least one column volume (CV). For example, about 1 CV or more (e.g., about 1, 2, 3, 4, 5, or more CVs) may be used for each solution that is applied to the column resin. However, it should be appreciated that any suitable column volume (e.g., less than 1, 1-5, or more than 5) can be used. It also should be appreciated that the same volume of each solution can be used or different volumes of one or more solutions can be used, as aspects of the invention are not limited in this respect.

The column can be washed with the reducing solution followed by the chaotropic solution until no or essentially no protein further elutes from the column Eluate from chromatography columns can be monitored by UV absorbance or by analysis of the eluate and/or resin by gel electrophoresis or any other method known to those of skill in the art. For instance, U.S. Pat. No. 6,972,327 describes various methods for regenerating a column based on chaotropic solutions that include a reducing agent, and is incorporated by reference.

In some embodiments, chromatography material (e.g., chromatography resin) can be regenerated in the context of a column, for example, by washing the column using one or more solutions as described herein. In some embodiments, chromatography material (e.g., chromatography resin) can be regenerated in a bulk form (e.g., after unpacking a column or from any suitable source) using one or more solutions as described herein. In some embodiments, the regenerated chromatography material can be packed or repacked into a column.

Another aspect of the invention provides a method of eluting from a Protein A or Protein G chromatography resin an antibody or an Fc fusion protein that has been bound thereto, and regenerating the chromatography resin by washing the chromatography resin with a reducing solution followed by a chaotropic solution. In another related aspect, the invention provides a method of regenerating a Protein A or Protein G chromatography resin by washing the chromatography resin with a reducing solution followed by a chaotropic solution, and then, after washing the column with the solutions, re-using the clean chromatography resin for an additional round of purification. Accordingly, one can again bind an antibody or an Fc fusion protein to the Protein A or Protein G chromatography resin. In this aspect, the invention can further comprise eluting the antibody or the Fc fusion protein from the chromatography resin. Methods of eluting antibodies and Fc fusion proteins from such columns are well known in the art and include, for example, low pH or high pH elution conditions. In particular preferred embodiments, the antibody can be, for example, an antibody that immunospecifically recognize a human EGF receptor, a her-2/neu receptor, a CEA antigen, a Prostate Specific Membrane Antigen (PSMA), a CD5, a CD11a, a CD18, a NGF, a CD20, a CD25 (IL-2R, Tac), a CD33, a CD52, a GPIIbIIIa receptor, an Ep-cam, a TNF-alpha, a TGF-b1, a VEGF, an alpha 4 beta 7 integrin, an IgEs, a CMV protein. The Fc fusion protein can be an Fc domain covalently fused to a TNF receptor extracellular domain, a Flt3 ligand extracellular domain, or a RANK extracellular domain, to name just a few non-limiting examples.

It is expected that the methods of regenerating chromatography resins will be useful for other types of affinity resins besides Protein A and Protein G chromatography resins, particularly those affinity resins whose binding moieties do not contain disulfide bonds. For purposes of the invention, the term "affinity resins" excludes those resins that rely upon thiol binding such as glutathione resins for binding GST (glutathione S-transferase). Examples of affinity resins are avidin or streptavidin moieties, protein A, protein G, protein L, and sugar moiety resins (e.g., lectin chromatography resins). The inventive methods may also be used to regenerate ion exchange resins, size exclusion chromatography resins, and hydrophobic interaction chromatography resins, particularly on an industrial scale. By "industrial scale" is meant that the volume of chromatography resin used is at least about 1 liter, at least about 3 liters, at least about 6 liters, at least about 10 liters, at least about 50 liters, at least about 100 liters. In fact, the volume of chromatography resin used together in industrial scale processes can be as large as 300 to 500 liters.

In some embodiments, methods of the invention can be used in the purification of most proteins, including, but not limited to, proteins that bind to affinity resins such as, for example, protein A and/or protein G. A protein is generally understood to be a polypeptide of at least about 10 amino acids, for example at least about 25 amino acids, at least about 75 amino acids, or at least about 100 amino acids. However, it should be appreciated that aspects of the invention can be used for chromatography resins associated with the purification of any protein of interest, regardless of protein size, and regardless of the multimeric form of the protein (e.g., whether it is a monomer, homo- or hetero-dimer, homo- or hetero-trimer, or any other multimeric form as aspects of the invention are not limited in this respect).

Generally, methods of the invention are useful for the purification of therapeutic and/or recombinant proteins. Recombinant proteins are proteins produced by the process of genetic engineering. The term "genetic engineering" refers to any recombinant DNA or RNA method used to create a host cell that expresses a gene at elevated levels, at lowered levels, or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in Current Protocols in Molecular Biology, Ausubel et al., eds. (Wiley & Sons, New York, 1988, and quarterly updates) and Sambrook et al., Molecular Cloning: A Laboratory Manual (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96(6): 2758-63).

The proteins can be produced recombinantly in eukaryotic cells or prokaryotic cells. The proteins can be derived from genetically engineered plants, transgenic animals, or can be secreted by production cells adapted to grow in cell culture. Production cells can be bacterial (e.g., *E. coli, Streptomyces* spp., and *Bacillus* spp.), fungal (e.g., *Aspergillus*), invertebrate-derived (e.g., insect) or mammalian. Examples of mammalian cells commonly used in the industry are CHO, VERO, BHK, HeLa, CV 1 (including Cos), MDCK, 293, 3T3, myeloma cell lines (especially murine), PC12 and W138 cells. Particularly preferred host cells are Chinese hamster ovary (CHO) cells, which are widely used for the production of several complex recombinant proteins, e.g., cytokines, clotting factors, and antibodies (Brasel et al., 1996, Blood 88:2004-2012; Kaufman et al., 1988, J. Biol Chem 263: 6352-6362; McKinnon et al., 1991, J Mol Endocrinol 6:231-239; Wood et al., 1990, J. Immunol 145:3011-3016). The dihydrofolate reductase (DHFR)-deficient mutant cell line (Urlaub et al., 1980, Proc Natl Acad Sci USA 77:4216-4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527-566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

Proteins to be purified include protein-based drugs, also known as biologics. Preferably, the proteins are expressed as extracellular products. Proteins that can be purified using the methods of the invention include but are not limited to a Flt3 ligand, a CD40 ligand, erythropoietin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-beta, tumor necrosis factor, leukemia inhibitory factor, oncostatin-M, and various ligands for cell surface molecules Elk and Hek (such as the ligands for eph-related kinases, or LERKS). Descriptions of proteins that can be produced according to the inventive methods may be found in, for example, Human Cytokines: Handbook for Basic and Clinical Research, Vol. II (Aggarwal and Gutterman, eds. Blackwell Sciences, Cambridge Mass., 1998); Growth Factors: A Practical Approach (McKay and Leigh, eds., Oxford University Press Inc., New York, 1993) and The Cytokine Handbook (A W Thompson, ed.; Academic Press, San Diego Calif.; 1991).

Purification of the receptors for any of the aforementioned proteins can also be improved using the inventive methods, including the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such proteins are described in U.S. Pat. No. 5,767,064, which is incorporated herein by reference in its entirety.

Other proteins that can be produced using the inventive methods include cluster of differentiation antigens (referred to as CD proteins), for example, those disclosed in Leukocyte Typing VI (Proceedings of the VIth International Workshop and Conference; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Proteins that are enzymatically active can also be purified according to methods described herein. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active proteins can also be produced according to methods described herein.

Various fusion proteins can also be produced using the inventive methods. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (e.g., GM-CSF and IL-3, MGF and IL-3). Any of the above-enumerated molecules can be expressed as a fusion protein including but not limited to the extracellular domain of a cellular receptor molecule, an enzyme, a hormone, a cytokine, a portion of an immunoglobulin molecule, a zipper domain, and an epitope.

Generally, the inventive methods are useful for purification of proteins that bind to protein A and/or protein G resins. Such proteins include fusions of any of the above-enumerated molecules to a constant region portion of an antibody, immunoglobulin molecules or portions thereof, and chimeric antibodies (e.g., an antibody having a human constant region coupled to a murine antigen binding region) or fragments thereof.

Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., 1989, Biotechnology 7:934-938; Reichmann et al., 1988, Nature 332:323-327; Roberts et al., 1987, Nature 328:731-734; Verhoeyen et al., 1988, Science 239:1534-1536; Chaudhary et al., 1989, Nature 339:394-397). Preparations of fully human antibodies (such as are prepared using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al. EP 0 519 596 A1. For example, the invention can be used to in processes for the purification of human and/or humanized antibodies that immunospecifically recognize specific cellular targets, e.g., the human EGF receptor, the her-2/neu receptor, the CEA antigen, Prostate Specific Membrane Antigen (PSMA), CD5, CD11a, CD18, NGF, CD20, CD25 (IL-2R, Tac), CD33, CD52, GPIIbIIIa receptor, Ep-cam, other cancer cell surface molecules, TNF-alpha, TGF-b1, VEGF, other cytokines, alpha 4 beta 7 integrin, IgE, viral proteins (for example, cytomegalovirus and RSV), etc., to name just a few.

The resulting expressed polypeptide can then be purified, or partially purified, from such culture or component (e.g., from culture medium or cell extracts or bodily fluid) using known processes in combination with the methods of the invention. By "partially purified" means that some fractionation procedure, or procedures, have been carried out, but that more polypeptide species (at least 10%) than the desired protein is present. By "purified" is meant that the protein is essentially homogeneous, e.g., less than 1% contaminating proteins are present. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above. Any of the above chromatography resins can be regenerated using methods of the invention.

For example, in some aspects of the invention, the affinity purification steps can involve a Protein A or a Protein G affinity chromatography step, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety. The Protein A or Protein G affinity chromatography resin is then regenerated according to the methods provided herein. After regeneration, the resin can be used for another purification cycle.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Aspects of the invention also optionally encompass further formulating the proteins. By the term "formulating" is meant that a protein can be buffer exchanged, and/or stored and/or further processed to a sterile dosage form. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the protein, in combination with other components such as a physiologically acceptable diluent, carrier, or excipient. The term "pharmaceutically acceptable" means a non-toxic material that does not interfere with the effectiveness of the biological activity of the active ingredient(s).

Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Batch Screening Experiments

Figure 3:
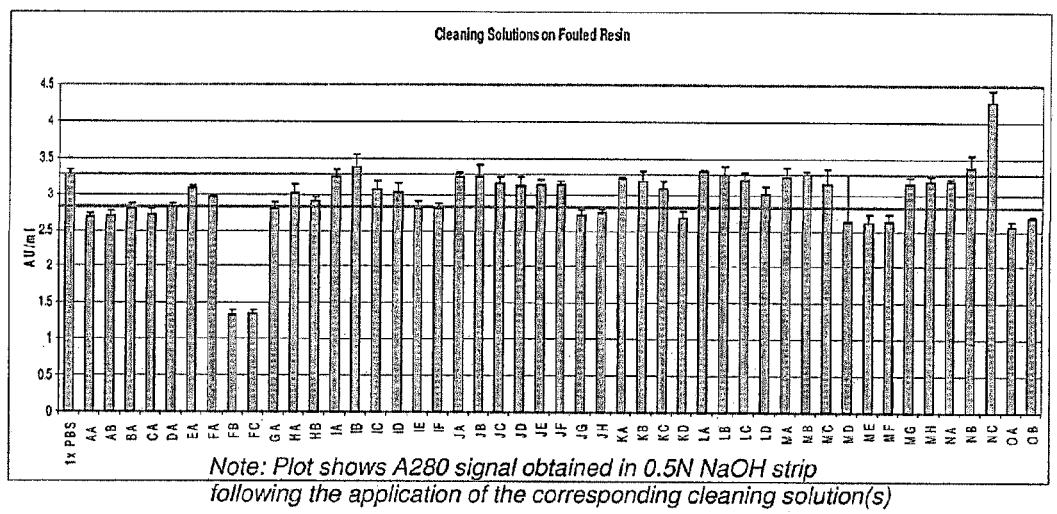
FIG. 3 provides an overview of batch screening experiments and shows that GuHCl (at >4M) had the highest cleaning efficacy, while limited differences were observed for the other cleaning solutions.
Figure 5:
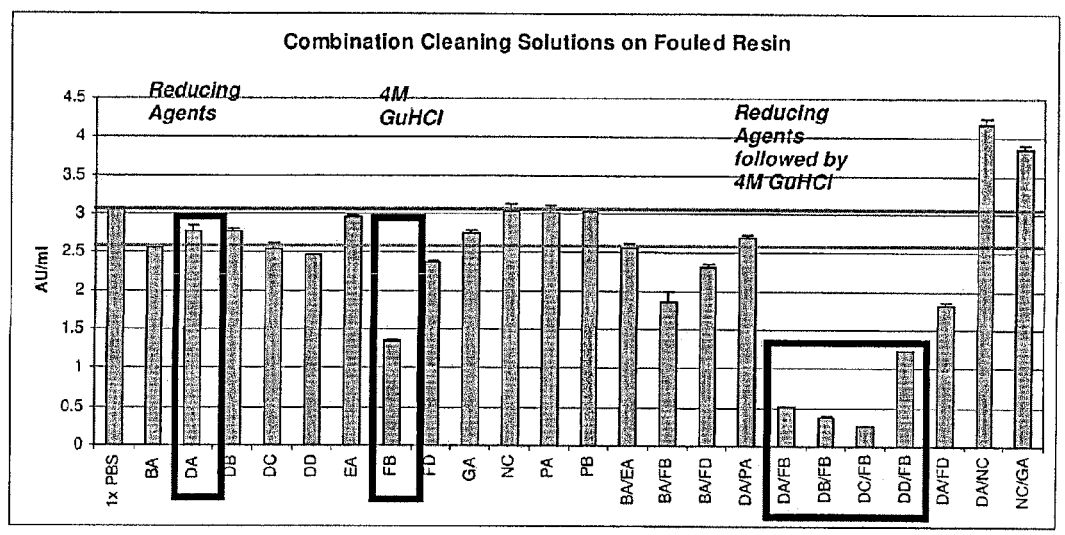
FIG. 5 provides an overview of batch screening experiments and shows that solutions of a reducing agent followed by a chaotropic agent showed a significant improvement in cleaning efficiency.
Figure 7:
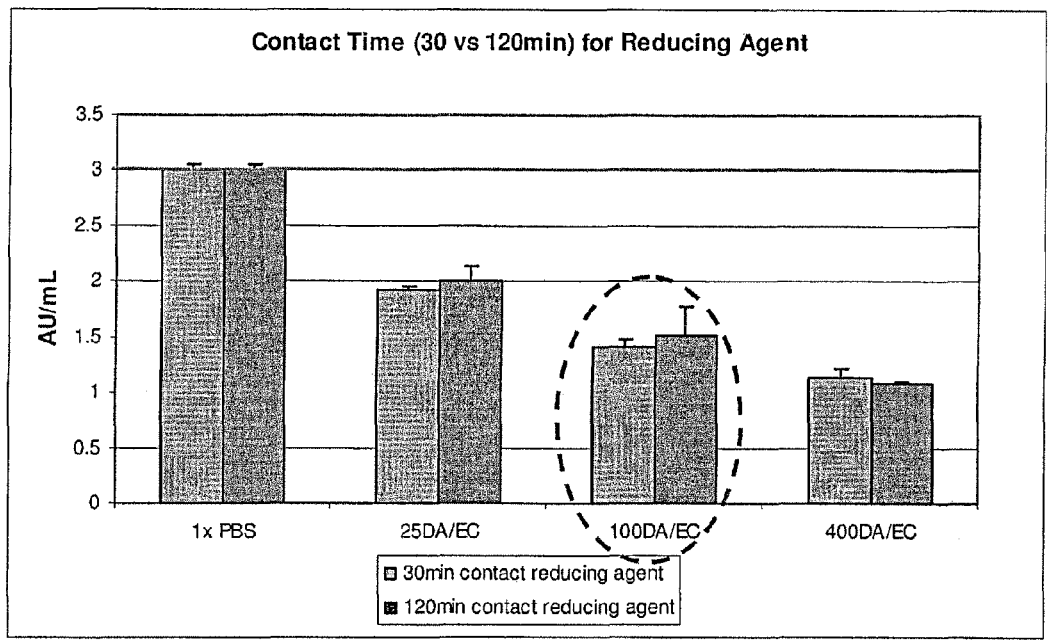
FIG. 7 provides an overview of batch screening experiments and shows the effect of thioglycerol contact time and concentration (as indicated by the effect of thioglycerol contact time and concentration of cleaning efficacy vs. fouled adsorbant).
Figure 8:
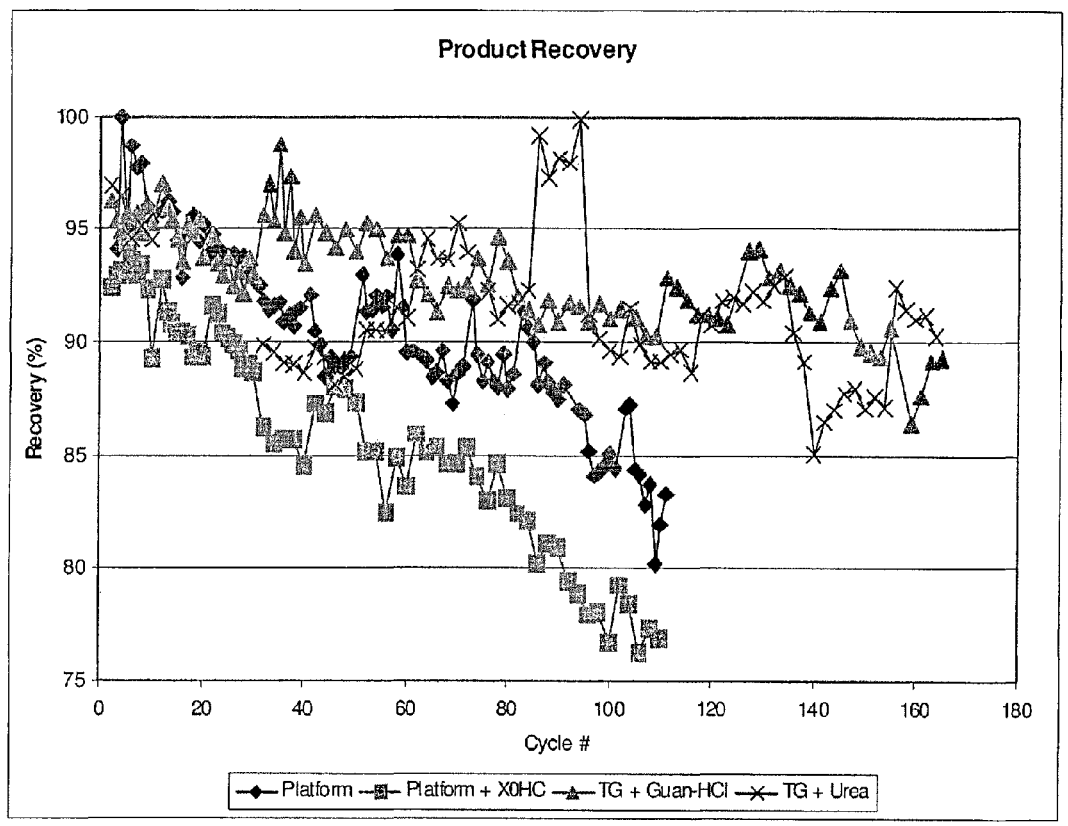
FIG. 8 shows the product recovery in a column cycling experiment.

Batch screening experiments were performed to determine the optimal regeneration regime including the determination of the nature of the cleaning solutions and the order of application of those solutions. The column was unpacked and an aliquot of the fouled adsorbent was added to the wells of a 96-well membrane bottomed plate (See FIG. 1). The absorbance of one of the strips is inversely proportional to the efficacy of the cleaning solution applied in the corresponding well. Cleaning parameters were optimized for solution composition including concentration and pH (See e.g., FIGS. 2, 3 and 6), the sequence of application of the various solutions (See e.g., FIGS. 4 and 5) and the incubation time (See FIG. 7) for concentrations between 25-400 mM. In general, solutions of a reducing agent followed by a chaotropic agent showed a significant improvement in cleaning efficacy.

Example 2

Column Cycling Experiments

Figure 9:
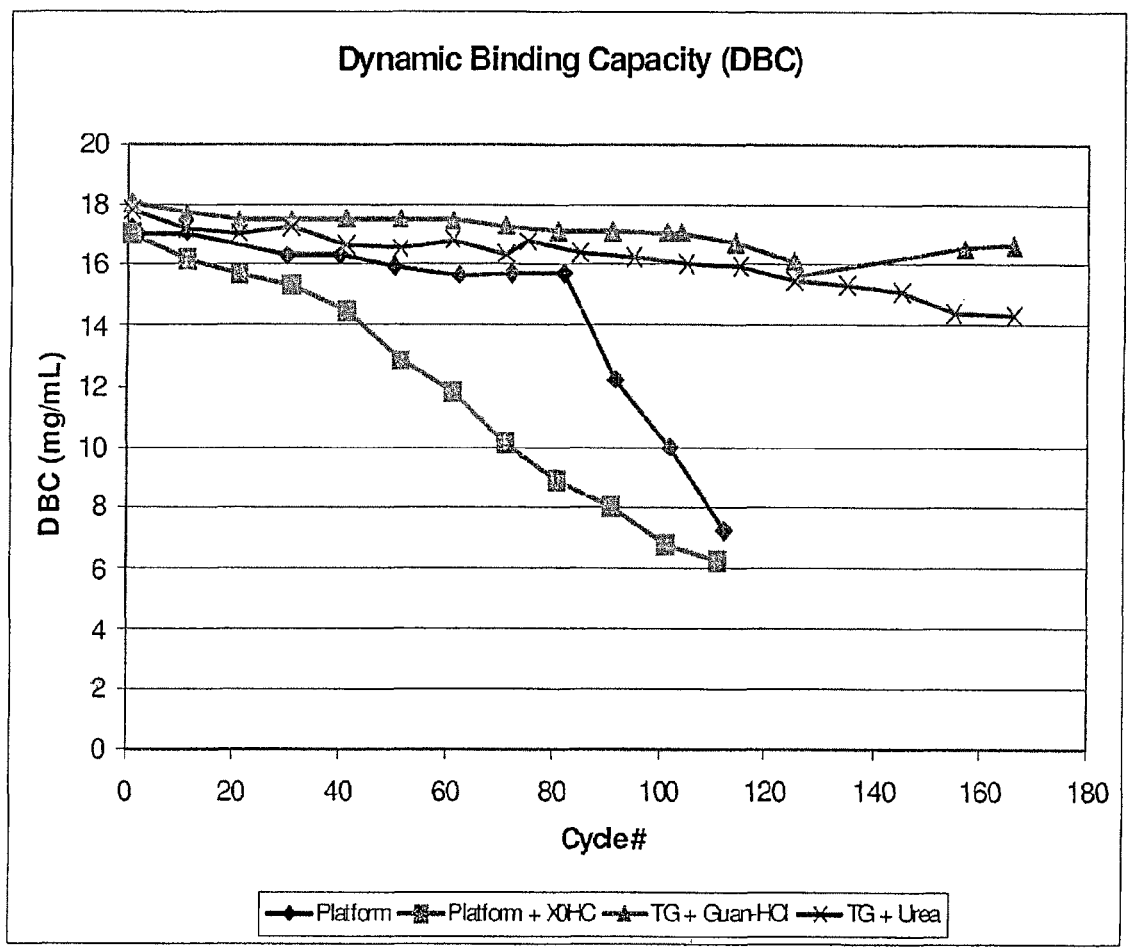
FIG. 9 shows the dynamic binding capacity in a column cycling experiment (TG: thioglycerol, X0HC: filter (Millipore).
Figure 10:
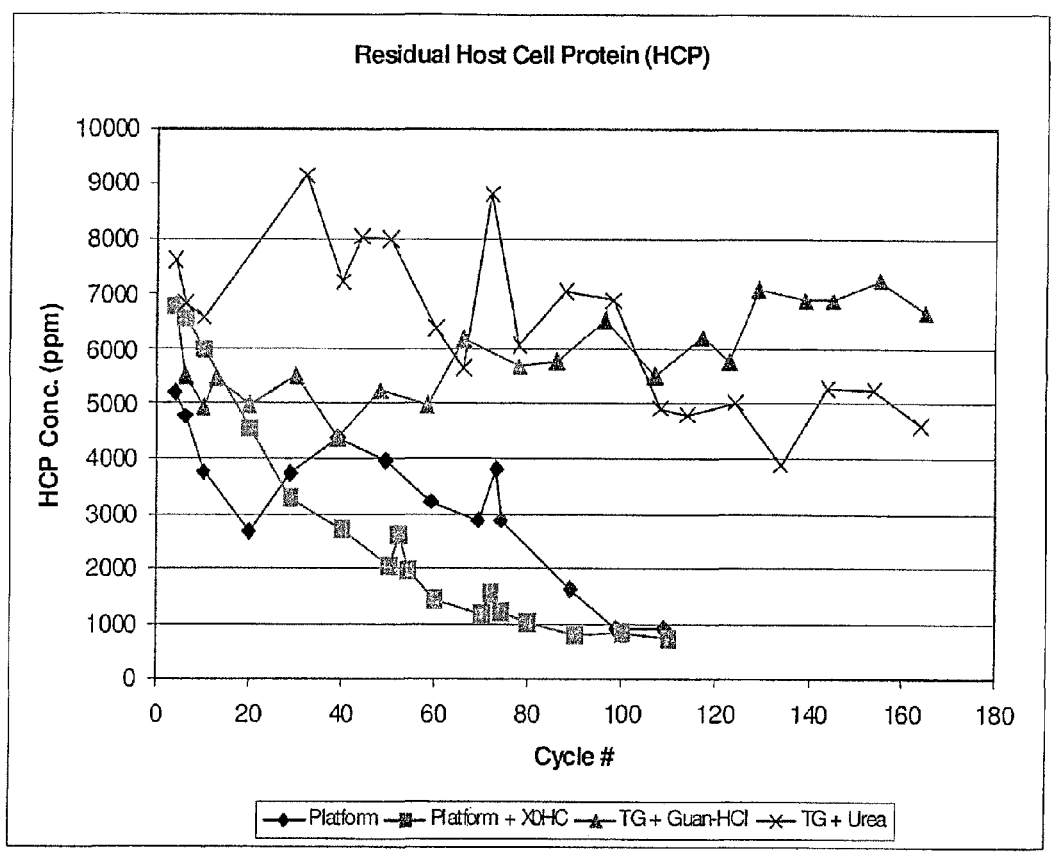
FIG. 10 shows the residual host cell proteins in a column cycling experiment.
Figure 11:
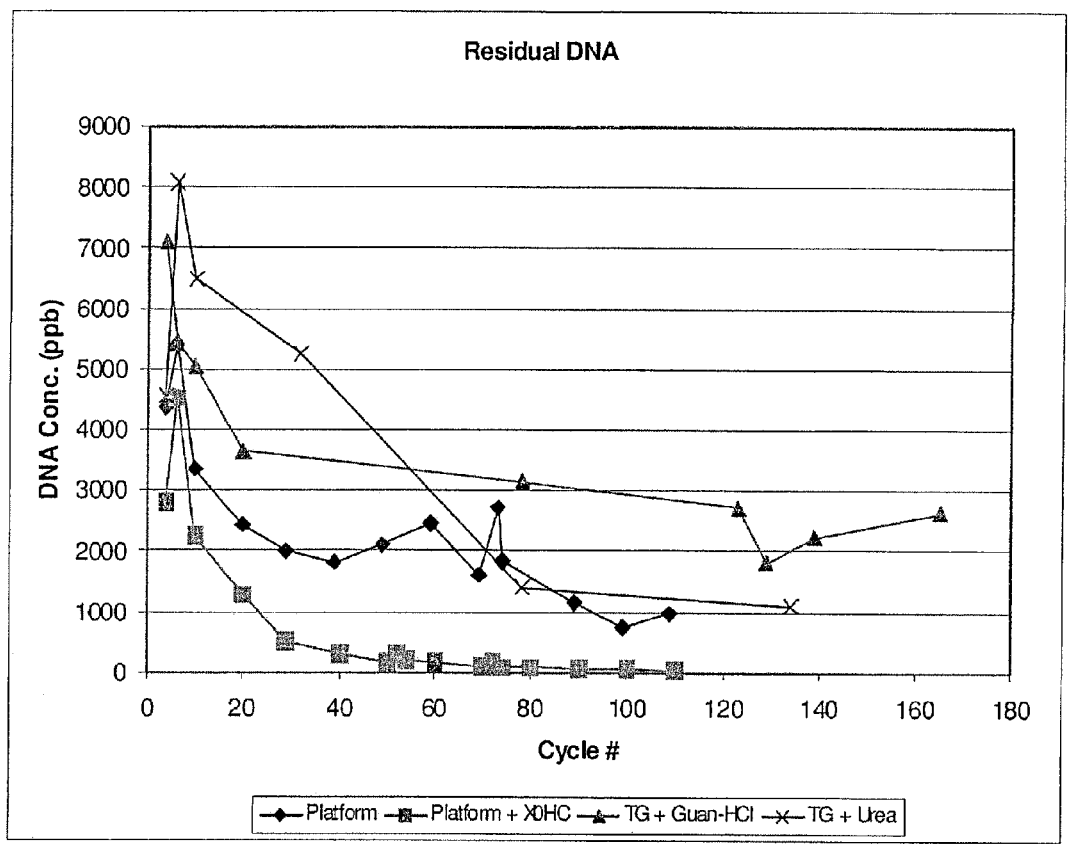
FIG. 11 shows the residual DNA in a column cycling experiment.
Figure 12:
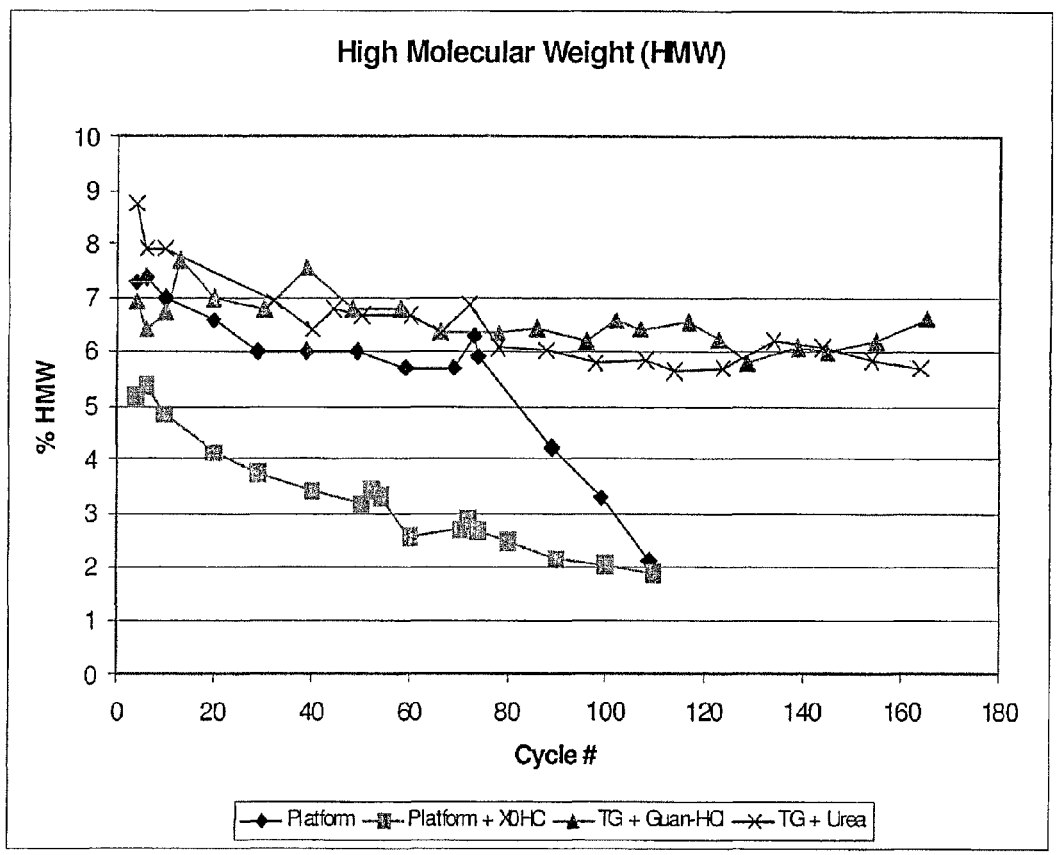
FIG. 12 shows the high molecular weight species in a column cycling experiment.
Figure 13:
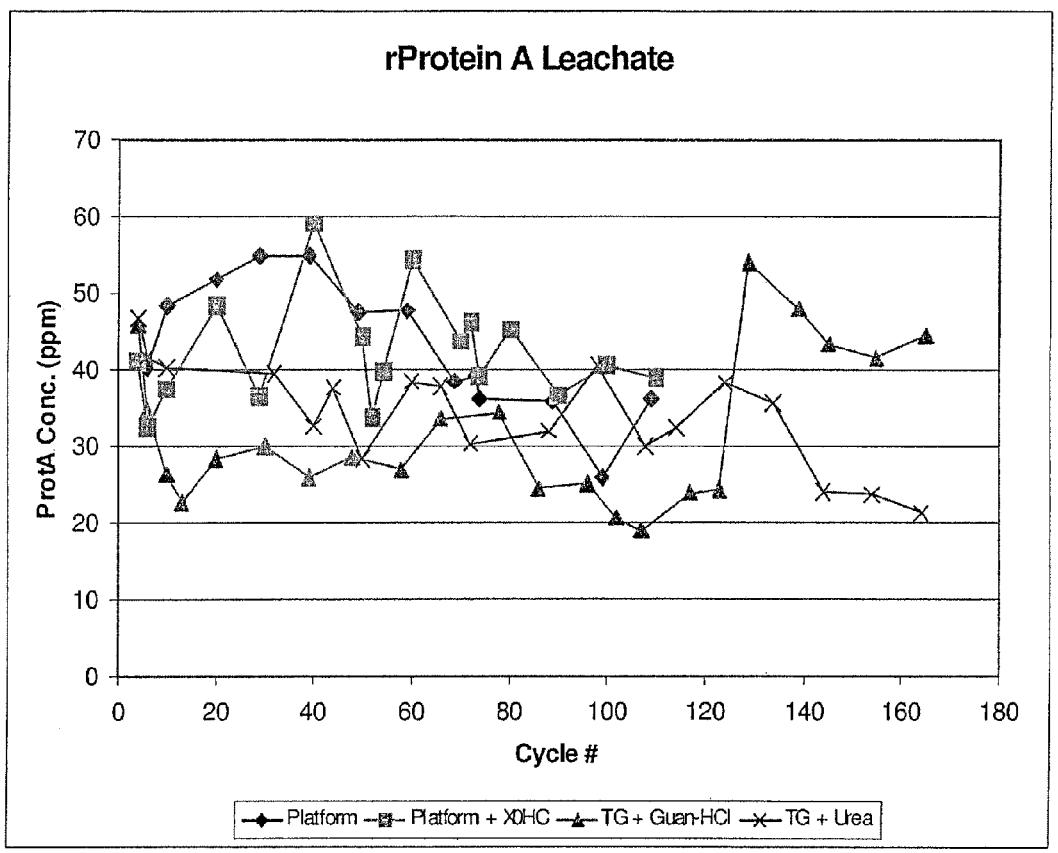
FIG. 13 shows the rProtein A leachate in a column cycling experiment.

A number of cycling experiments were performed to evaluate the protocols identified in the batch screening experiments for their long term impact. In a first study a cleaning regimen with 4M urea (3 CV, 30 mins) was evaluated. In a second study a cleaning regimen with X0HC filtration for load was evaluated (3 CV, 30 mins.). In a third study, a cleaning regimen of 100 mM thioglycerol (3 CV, 30 mins) followed by 4M GuHCL (3 CV, 30 mins., every other time) was evaluated. In a fourth study, a cleaning regimen of 100 mM thioglycerol (3 CV, 30 mins.) followed by 8M urea (3 CV, 30 mins., every other time) was evaluated. The results are depicted in FIGS. 8-13 (FIG. 8: product recovery; FIG. 9: dynamic binding capacity; FIG. 10 residual host cell proteins; FIG. 11: residual DNA; FIG. 12: high molecular weight species; FIG. 13: rProtein A leachate).

The experiments showed that the cleaning regimes enhanced the column lifetime by at least 2-3 fold (over 170 cycles vs. 60-75 cycles using platform cleaning). (Platform cleaning uses a wash with 0.85% phosphoric acid followed by a wash with a buffered solution containing 4M urea). In addition, the cleaning regimen provided more consistent product quality over the lifetime of the column.

Example 3

High Throughput Screening of Cleaning Solutions

Figure 14:
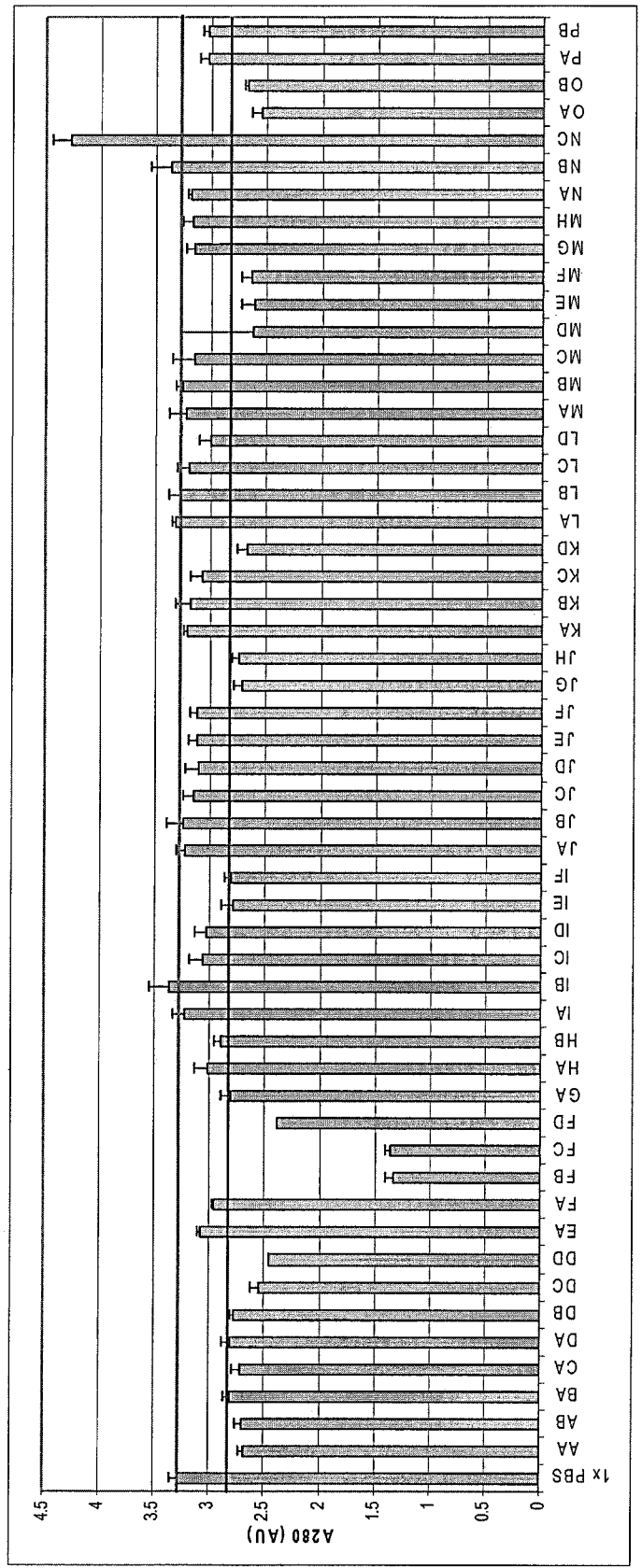
FIG. 14 shows the cleaning efficiency of the tested solutions. The cleaning efficacy of each solution is inversely proportional to the magnitude of the absorbance signal in the plot. The top line represents the level of cleaning by 1X PBS (control). The lower line represents the cleaning efficacy provided by the current platform acid strip solution (0.85% phosphoric acid).

A 96-well plate based high-throughput screening technique was employed to rank several different cleaning solutions and combinations thereof. A column packed with rProtein A adsorbent (Prosep Ultra Plus) was initially fouled by performing 75 purification cycles for an Fc fusion protein with minimal cleaning. The column was subsequently unpacked and the fouled adsorbent was transferred into 96-well membrane bottomed plates. Each well on the plate was packed with 80 μL of a 50% slurry of fouled adsorbent in storage buffer (1CV=40 μL). The following set of cleaning solutions was initially evaluated to identify lead cleaning agents for further optimization (See Table 1). 1X PBS solution was employed as a control representing no significant cleaning effect. 2×4 CV washes of each cleaning solution was separately applied to a set of wells (i.e., replicates) containing fouled adsorbent with a 30 min total contact time. Subsequently, the cleaned adsorbent was stripped with 0.5M NaOH caustic solution to strip any residual foulant not removed by the preceding cleaning solution washes. Thus, the average absorbance at 280 nm of the strip samples was inversely proportional to the cleaning efficacy of the corresponding cleaning solution, which enabled the relative ranking of the various cleaning solutions (See FIG. 14).

TABLE 1

List of Cleaning Solutions (lead candidates shown in Italic font):

| | |
|---|---|
| AA: | 0.1M Na Citrate, pH 2.5 |
| AB: | 0.2M Na Citrate, pH 2.0 |
| BA: | 0.85% Phosphoric Acid, pH 1.5 |
| CA: | 15 mM Phosphoric acid/0.5M NaCl, pH 2.0 |
| DA: | 100 mM thioglycerol, pH 3.7 |
| DB: | 100 mM 2-BME, pH 5.0 |
| DC: | 100 mM DTT, pH 4.5 |
| DD: | 100 mM L-glutathione reduced, pH 3.0 |
| EA: | 4M Urea/50 mM Na Acetate, pH 5.0 |
| EB: | 6M Urea/50 mM Na Acetate, pH 5.0# |
| EC: | 8M Urea/50 mM Na Acetate, pH 5.0# |
| FA: | 2M Guanidine-HCl, pH 6.5 |
| FB: | 4M Guanidine-HCl, pH 6.5 |
| FC: | 6M Guanidine-HCl, pH 6.7 |
| FD: | 4M Guanidine acetate, pH 5.8 |
| GA: | 120 mM Phosphoric acid/167 mM Acetic acid/2.2% Benzyl alcohol, pH 1.6 |
| HA: | 20% Ethanol/0.5M Acetic acid, pH 2.7 |
| HB: | 20% Ethanol/2.0M Acetic acid, pH 2.4 |
| IA: | 10% hexylene glycol |
| IB: | 20% hexylene glycol |
| IC: | 10% hexylene glycol/0.5M NaCl |
| ID: | 20% hexylene glycol/0.5M NaCl |
| IE: | 10% hexylene glycol/0.2M Na Citrate, pH 2.0 |
| IF: | 20% hexylene glycol/0.2M Na Citrate, pH 2.0 |
| JA: | 10% propylene glycol |
| JB: | 20% propylene glycol |
| JD: | 20% propylene glycol/0.5M NaCl |
| JC: | 10% propylene glycol/0.5M NaCl |
| JE: | 10% propylene glycol/1.0M NaCl |
| JF: | 20% propylene glycol/1.0M NaCl |
| JG: | 10% propylene glycol/0.2M Na Citrate, pH 2.0 |
| JH: | 20% propylene glycol/0.2M Na Citrate, pH 2.0 |
| KA: | 12% PEG 400 |
| KB: | 12% PEG 400/0.5M NaCl |
| KC: | 12% PEG 400/1.0M NaCl |
| KD: | 12% PEG 400/0.2M Na Citrate, pH 2.0 |
| LA: | 12% PEG 8000 |
| LB: | 12% PEG 8000/0.5M NaCl |
| LC: | 12% PEG 8000/1.0M NaCl |
| LD: | 12% PEG 8000/0.2M Na Citrate, pH 2.0 |
| MA: | 0.5% Tween-20 |
| MB: | 1.0% Tween-20 |
| MC: | 0.5% Tween-20/1M NaCl |
| MD: | 1.0% Tween-20/1M NaCl |
| ME: | 0.5% Tween-20/0.2M Na Citrate, pH 2.0 |
| MF: | 1.0% Tween-20/0.2M Na Citrate, pH 2.0 |
| MG: | 0.5% Tween-20/0.5M Na Acetate, pH 4.6 |
| MH: | 1.0% Tween-20/0.5M Na Acetate, pH 4.6 |
| NA: | 1.0% Triton X-100 |
| NB: | 1.0% Triton X-100/1M NaCl |
| NC: | 1.0% Triton X-100/0.2M Na Citrate, pH 2.0 |
| OA: | 0.5% Tween-80/0.2M Na Citrate, pH 2.0 |
| OB: | 1.0% Tween-80/0.2M Na Citrate, pH 2.0 |

TABLE 1-continued

List of Cleaning Solutions (lead candidates shown in Italic font):

PA:  0.5M L-Arginine, pH 6.8
PB:  2M L-Arginine, pH 6.9

Not tested individually

Figure 15:
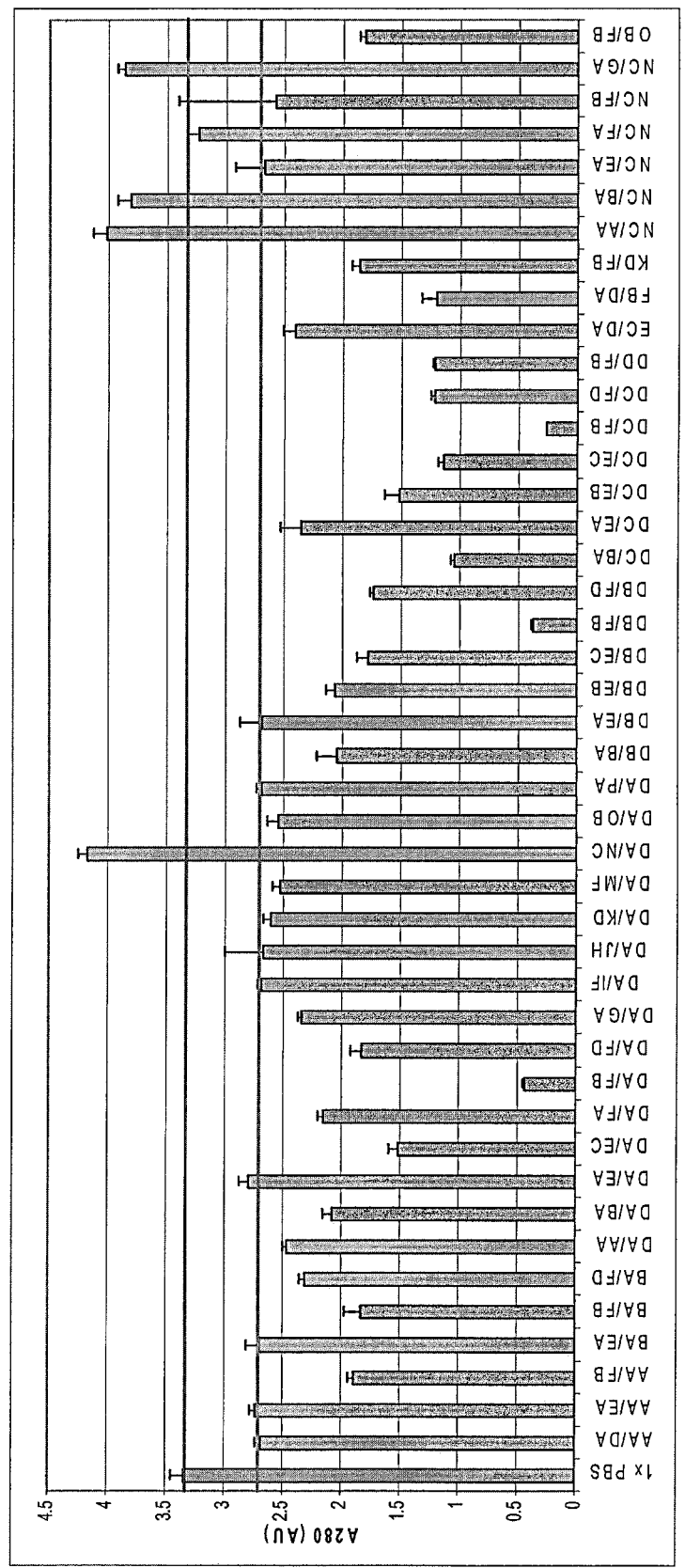
FIG. 15 shows the cleaning efficiency of the tested solution combinations. The cleaning efficacy of each solution combination is inversely proportional to the magnitude of the absorbance signal in the plot. The top line represents the level of cleaning by 1X PBS (control). The lower line represents the cleaning efficacy provided by the current platform cleaning regimen (0.85% phosphoric acid wash followed by a 4M Urea solution wash).

Solutions that had cleaning efficacy comparable to or better than the 0.85% phosphoric acid strip solution were identified as leads for further evaluation. Select sequential combinations of these solutions were evaluated to determine if these provided enhanced cleaning efficacy over the individual solutions (See FIG. 15).

The results showed that combinations containing 4M guanidine hydrochloride showed better cleaning efficacy than the platform cleaning regimen. Furthermore, regimens combining a reducing agent wash followed by a chaotropic agent wash provided better cleaning efficacy than the corresponding reducing agent or chaotropic agent alone. The order of application of the two solutions in this enhanced cleaning regimen was also shown to be significant, with the regimen with the order switched having a lower cleaning efficacy.

Figure 16:
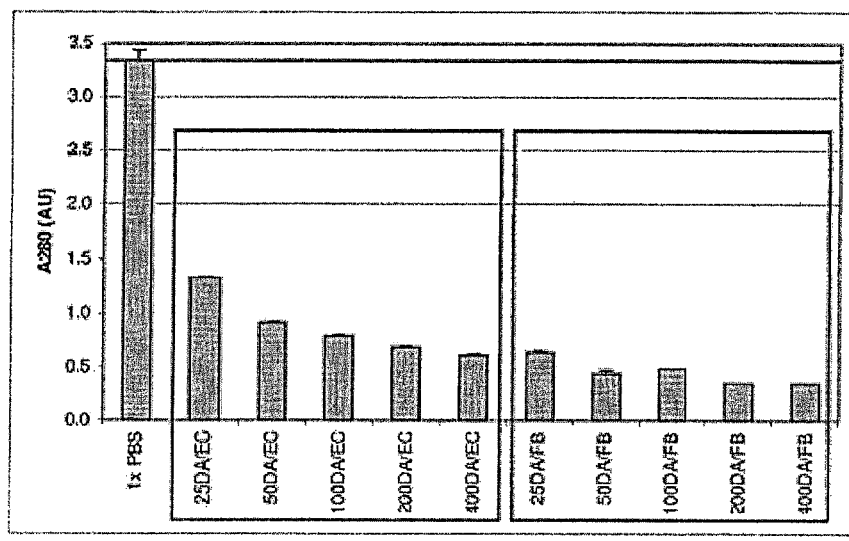
FIG. 16 shows the cleaning efficiency for different concentrations of thioglycerol.

For the purpose of demonstration of proof of concept, 8 M Urea (EC) and 4M guanidine hydrochloride (FB) were selected as representative chaotropic agents. 1-thioglycerol was selected as the reducing agent and batch experiments were performed to optimize the concentration of 1-thioglycerol. 1-thioglycerol concentrations between 25-400 mM were examined. Only marginal improvements in cleaning efficacy were observed for 1-thioglycerol concentration ≥50 mM. Therefore, a 100 mM thioglycerol solution (DA) was selected as the optimal concentration (See FIG. 16).

Figure 17:
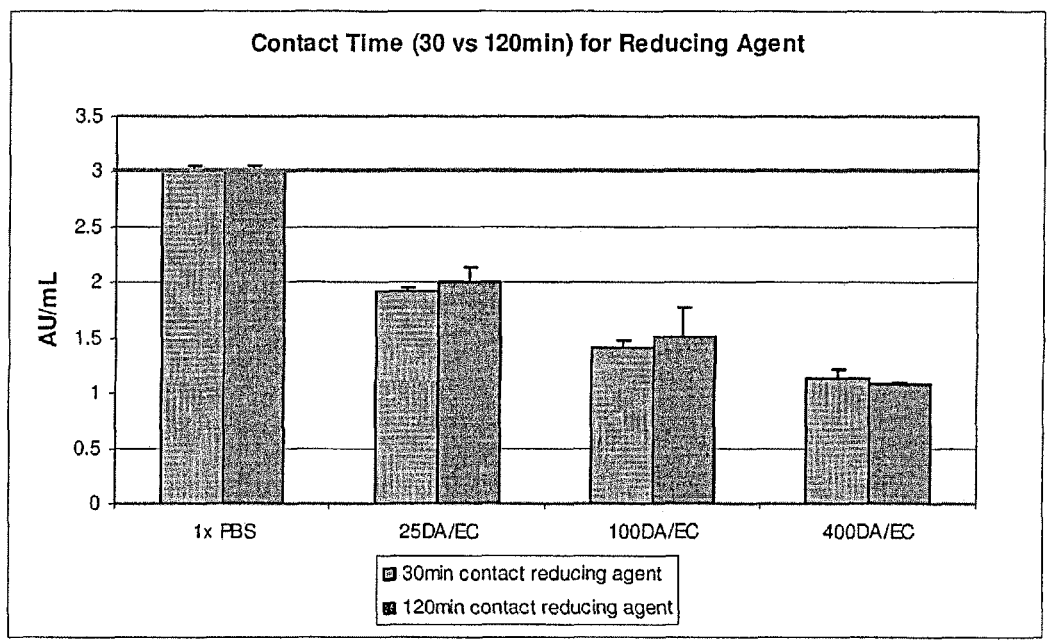
FIG. 17 shows the cleaning efficiency for different contacting times of the reducing agent.

Finally, the effect of contact time of the reducing agent was evaluated as a function of concentration. The results showed no significant difference in cleaning efficacy by increasing the contact time from 30 min to 120 mM (See FIG. 17).

Example 4

Column Cycling Studies

Based on the results of the batch screening experiments, column cycling studies were performed in order to obtain a true assessment of the column cleaning efficacy of an example of an enhanced cleaning regimen compared to a platform cleaning regimen. To this end, the following studies were performed:

Cycling Study #1: Platform cleaning regimen i.e., 0.85% Phosphoric acid (3 CV for 30 min) followed by 4M Urea (3 CV)

Cycling Study #2: Strip with 0.85% Phosphoric acid (3 CV for 30 min) every cycle and regeneration with 100 mM 1-thioglycerol (3CV for 30 min) followed by 4M guanidine hydrochloride (3 CV for 30 min) every other cycle Cycling Study #3: Strip with 0.85% Phosphoric acid (3 CV for 30 min) every cycle and regeneration with 100 mM 1-thioglycerol (3 CV for 30 min) followed by 8M Urea (3 CV for 30 min) every other cycle The product recovery, dynamic binding capacity, and product quality were tracked throughout each cycling study to determine the trends in these parameters throughout the column lifetime.

Figure 18:
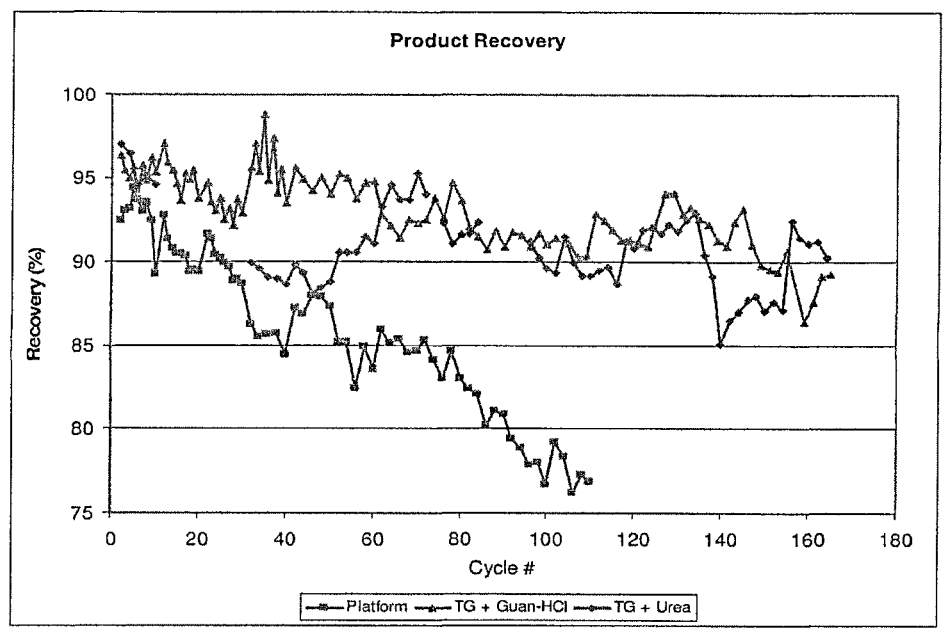
FIG. 18 shows the recovery percentage as a function of the number of cycles.

As shown in FIG. 18, the product recovery rapidly decreased with increasing cycle count for the platform cleaning regimen and the study was terminated at 110 cycles. On the other hand, the enhanced cleaning regimen provided more consistent product yields through ~165 cycles.

Figure 19:
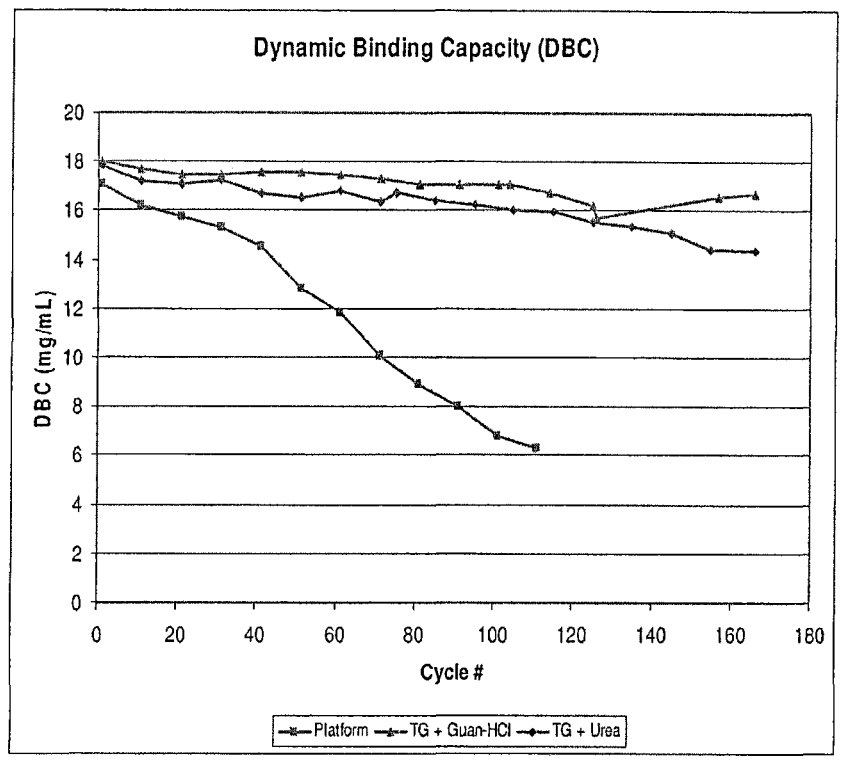
FIG. 19 shows the dynamic binding capacity as a function of the number of cycles.

The dynamic binding capacity of the column dropped rapidly when the platform regimen was employed for cleaning the column, decreasing by ~50% over 81 cycles. The use of the enhanced cleaning regimen resulted in a significantly slower rate of decline of binding capacity, with the DBC dropping by ≤15% over ~165 cycles (See FIG. 19).

Figure 20:
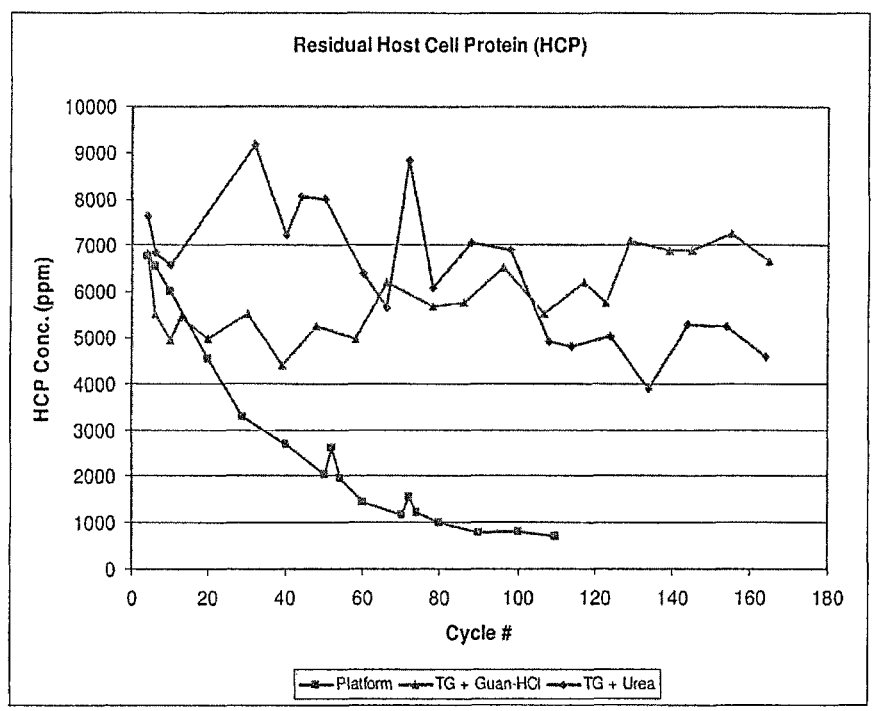
FIG. 20 shows the residual host cell protein as a function of the number of cycles.

Also, the use of the enhanced cleaning regimen resulted in more consistent product quality between cycles as compared to the use of the platform cleaning regimen. For example, host cell protein (HCP) levels in the column eluate dropped by ~90% over 110 cycles when platform cleaning was employed. On the other hand, the variation in HCP levels was generally within the limits of assay variability over ~165 cycles with the enhanced cleaning regimen. Similar trends were observed for other product quality attributes such as host cell DNA and high molecular weight (HMW) species (See FIG. 20).

Thus, an enhanced cleaning regimen comprising of a reducing agent (1-thioglycerol, in this specific case) followed by a chaotropic agent (such as urea or guanidine hydrochloride) provided significant improvement in column cleaning resulting in improved product capacity and yield as well as more consistent product quality over the column lifetime.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. A method for regenerating an antibody binding resin, the method comprising:
a first step of washing an antibody binding resin with a reducing solution, followed by a second step of washing the antibody binding resin with a chaotropic solution, thereby regenerating the antibody binding resin, wherein the first step and the second step are performed separately.

2. The method of claim 1, further comprising a step of washing the antibody binding resin with an equilibration buffer, wherein the step of washing with the equilibration buffer is a separate step that is performed after the first washing step and prior to the second washing step.

3. The method of claim 2, wherein the equilibration buffer is selected from the group consisting of phosphate buffers and carbonate buffers.

4. The method of claim 3, wherein the equilibration buffer is a phosphate buffer.

5. The method of claim 1, further comprising washing the antibody binding resin with an acidic solution, wherein the step of washing with the acidic solution is a separate step that is performed prior to the first washing step.

6. The method of claim 5, wherein the acidic solution is selected from the group consisting of phosphoric acid and acidic acid.

7. The method of claim 6, wherein the acidic solution is phosphoric acid.

8. The method of claim 5, further comprising washing the antibody binding resin with a neutralizing solution, wherein the step of washing with the neutralizing solution is a separate step that is performed after the step of washing with the acidic solution and prior to the first washing step.

9. The method of claim 8, wherein the neutralizing solution is selected from the group consisting of phosphate buffers, weak acids and weak bases.

10. The method of claim 9, wherein the neutralizing solution is a phosphate buffer.

11. The method of claim 1, further comprising using the antibody binding resin to purify an antibody.

12. The method of claim 1, further comprising repeating the first and second washing steps.

13. The method of claim 1, wherein the reducing solution includes a reducing agent selected from the group consisting of thioglycerol, 1-4,-dithiothreitol, and 2-mercaptoethanol.

14. The method of claim 13, wherein the reducing agent is thioglycerol.

15. The method of claim 1, wherein the chaotropic solution includes a chaotropic agent selected from the group consisting of guanidine HCl, urea, and guanidine acetate.

16. The method of claim 15, wherein the chaotropic agent is guanidine HCl or urea.

17. The method of claim 1, wherein the antibody binding resin is selected from the group consisting of a protein A resin and a protein G resin.

18. The method of claim 17, wherein the antibody binding resin is a protein A resin.

19. A method for regenerating an antibody binding resin, the method comprising the following ordered steps:
(a) a first step of washing an antibody binding resin with a reducing solution selected from the group consisting of thioglycerol, 1-4,-dithiothreitol, and 2-mercaptoethanol;
(b) a second step of washing the antibody binding resin with an equilibration buffer selected from the group consisting of phosphate buffers and carbonate buffers; and
(c) a third step of washing the antibody binding resin with a chaotropic solution selected from the group consisting of guanidine HCl, urea, and guanidine acetate, thereby regenerating the antibody binding resin.

20. The method of claim 19, wherein the reducing agent is thioglycerol.

21. The method of claim 19, wherein the chaotropic agent is guanidine HCl or urea.

22. The method of claim 19, wherein the equilibration buffer is a phosphate buffer.

* * * * *